(12) United States Patent
Schmitt et al.

(10) Patent No.: US 7,940,377 B1
(45) Date of Patent: May 10, 2011

(54) PASSIVE BACKGROUND CORRECTION METHOD FOR SPATIALLY RESOLVED DETECTION

(75) Inventors: Randal L. Schmitt, Tijeras, NM (US); Philip J. Hargis, Jr., Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 273 days.

(21) Appl. No.: 12/329,031

(22) Filed: Dec. 5, 2008

(51) Int. Cl.
*G01C 3/08* (2006.01)
(52) U.S. Cl. ............. 356/5.01; 356/3.01; 356/4.01; 356/4.1; 356/5.1
(58) Field of Classification Search ........... 356/3.01–22, 356/28, 28.5
See application file for complete search history.

(56) References Cited

U.S. PATENT DOCUMENTS

| | | | |
|---|---|---|---|
| 5,022,755 A | 6/1991 | Wells et al. | |
| 5,450,125 A | 9/1995 | Ulich et al. | |
| 6,055,329 A * | 4/2000 | Mufti | 382/152 |
| 6,943,353 B2 | 9/2005 | Elmore et al. | |
| 7,164,787 B1 | 1/2007 | Nevis et al. | |
| 7,164,788 B1 | 1/2007 | Nevis et al. | |
| 7,203,339 B1 | 4/2007 | Nevis et al. | |
| 2002/0071122 A1* | 6/2002 | Kulp et al. | 356/437 |
| 2005/0162638 A1* | 7/2005 | Suzuki et al. | 356/4.04 |

* cited by examiner

*Primary Examiner* — Thomas H Tarcza
*Assistant Examiner* — Luke D Ratcliffe
(74) *Attorney, Agent, or Firm* — Carol I. Ashby (57) ABSTRACT

A method for passive background correction during spatially or angularly resolved detection of emission that is based on the simultaneous acquisition of both the passive background spectrum and the spectrum of the target of interest.

16 Claims, 8 Drawing Sheets

PASSIVE BACKGROUND CORRECTION METHOD FOR SPATIALLY RESOLVED DETECTION

The United States Government has rights in this invention pursuant to Department of Energy Contract No. DE-AC04-94AL85000 with Sandia Corporation.

BACKGROUND OF THE INVENTION

This invention relates to a method for improved passive background subtraction using spatially resolved detection systems.

Active remote sensing systems transmit a photoexcitation light pulse such as a laser pulse through the atmosphere, collect backscattered and fluorescent emission generated by interaction of the photoexcitation light with a target, and spectrally and temporally resolve the collected light. Computer algorithms are used to process the collected spectral data to discriminate between species of interest, interfering species, and passive background spectra. Often the spectral signal from a species of interest is relatively weak. Proper detection then requires accurate subtraction of passive background light contributions to the measured spectra. Passive background light is light from sources such as solar radiation and artificial lighting where the light is not generated as a consequence of interaction with the photoexcitation light. Passive background light can include any light that is not generated by interaction of the photoexcitation light with a target.

In many remote sensing systems, a spectrum of the passive background is collected between laser shots. This background is subtracted from the "active" spectrum corresponding to the laser-excited emission before the analysis algorithms are employed to determine whether or not a species of interest is present. One significant problem with interleaving the passive background data acquisition with the acquisition of spectra from the desired target is that the intensity of passive lighting sources often changes even on the short timescale typically found between laser pulses. One example is artificial lighting (for example, from Hg-vapor or Na-vapor lamps) which exhibits a 60 Hz half-wave rectified intensity variation that is frequently not synchronized with the laser pulses from a LIDAR system. This leads to increased uncertainty in the magnitude of the actual signal that may be originating from the target of interest. This present invention addresses the problem of passive background correction.

BRIEF DESCRIPTION OF THE DRAWINGS

The accompanying drawings, which are incorporated in and form part of the specification, illustrate some embodiments of the present invention and, together with the description, serve to explain the principles of the invention.

FIG. 11 illustrates a) the passive background as a function of wavelength obtained by summing rows receiving only background illumination, and b) the signal obtained by subtracting a scaled passive background such as that shown in a) from the summation of the rows receiving both background and excitation-beam-induced signal.

DETAILED DESCRIPTION OF THE INVENTION

This invention comprises a method for passive background correction during spatially or angularly resolved detection of emission that is based on the simultaneous acquisition of both the passive background spectrum and the spectrum of the target of interest. For purposes of the description of embodiments of the invention, the term simultaneous refers to events and actions occurring within approximately the time corresponding to a readout cycle of a pixelated detector array or to a round-trip transit time of a single laser pulse to a remote target and back to the receiver optical system. For the purposes of description, the terms laser light, laser beam, and laser pulse are employed for convenience, but it is to be understood that other collimated light sources with beam divergence angles less than the field-of-view angle of the receiver optical system may also be used. For the purposes of this invention, a target can comprise a solid, a liquid, or a gas; it can comprise a pure chemical species or a mixture of species. In some embodiments, the target can be a solid surface or an aerosol.

Embodiments of this invention avoid the problem of variation in background illumination of the detector array between the time when a signal corresponding to a laser pulse is generated and received and the time when a background spectrum is normally taken in the time interval between laser pulses; this is achieved by simultaneously measuring passive background illumination and light coming from the laser-excited volume that can be distinguished because they are received by different pixels and/or sets of pixels of the detector array. The light coming from the laser-excited volume contains contributions from both the passive background illumination and the light generated from the target by interaction with the laser light. The embodiments employ the difference in the greater angular dispersion of the passive background light compared to the target signal, which has an angular dispersion determined by the divergence of the laser beam or other highly collimated light source generating the signal. The narrower range of angles associated with the laser-generated signal results in a section of the detector array receiving target-related signal while pixels outside that section of the detector array receive background light from a wider range of field angles as determined by the field of view of the receiver optical system. By assigning pixels to target-signal and background-signal groupings, it is possible to determine both background and target signal values during a single detector array read-out cycle or during a single laser pulse. Because embodiments of this invention record background-only and target-signal-plus-background at the same time, detector readout time does not limit the fidelity of background subtraction in the way that it can in conventional measurement approaches that interleave signal-plus-background and background image measurements, for which detector readout time may set the minimum time difference between the acquisition of the signal-plus-background and background-only data.

Figure 1:
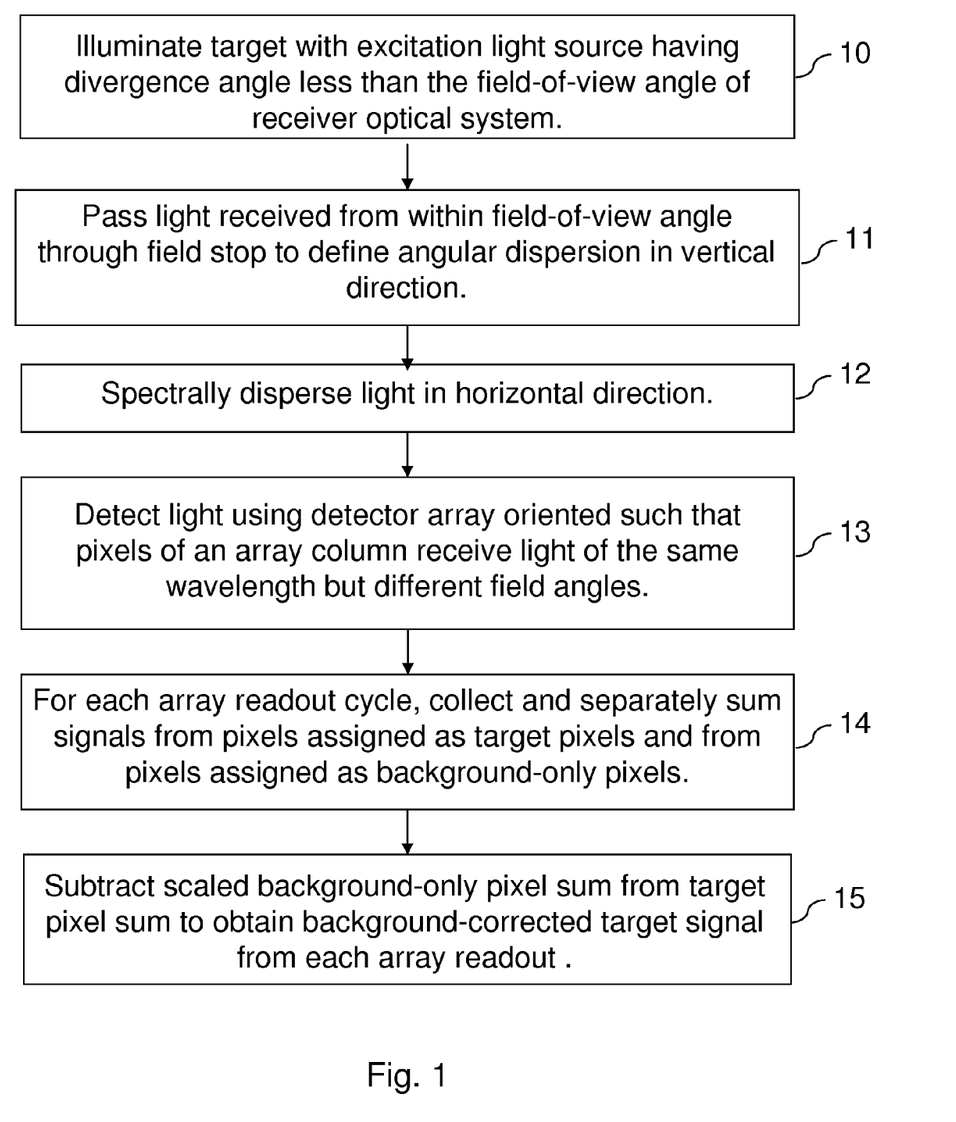
FIG. 1 illustrates one embodiment of the method of this invention.
Figure 2:
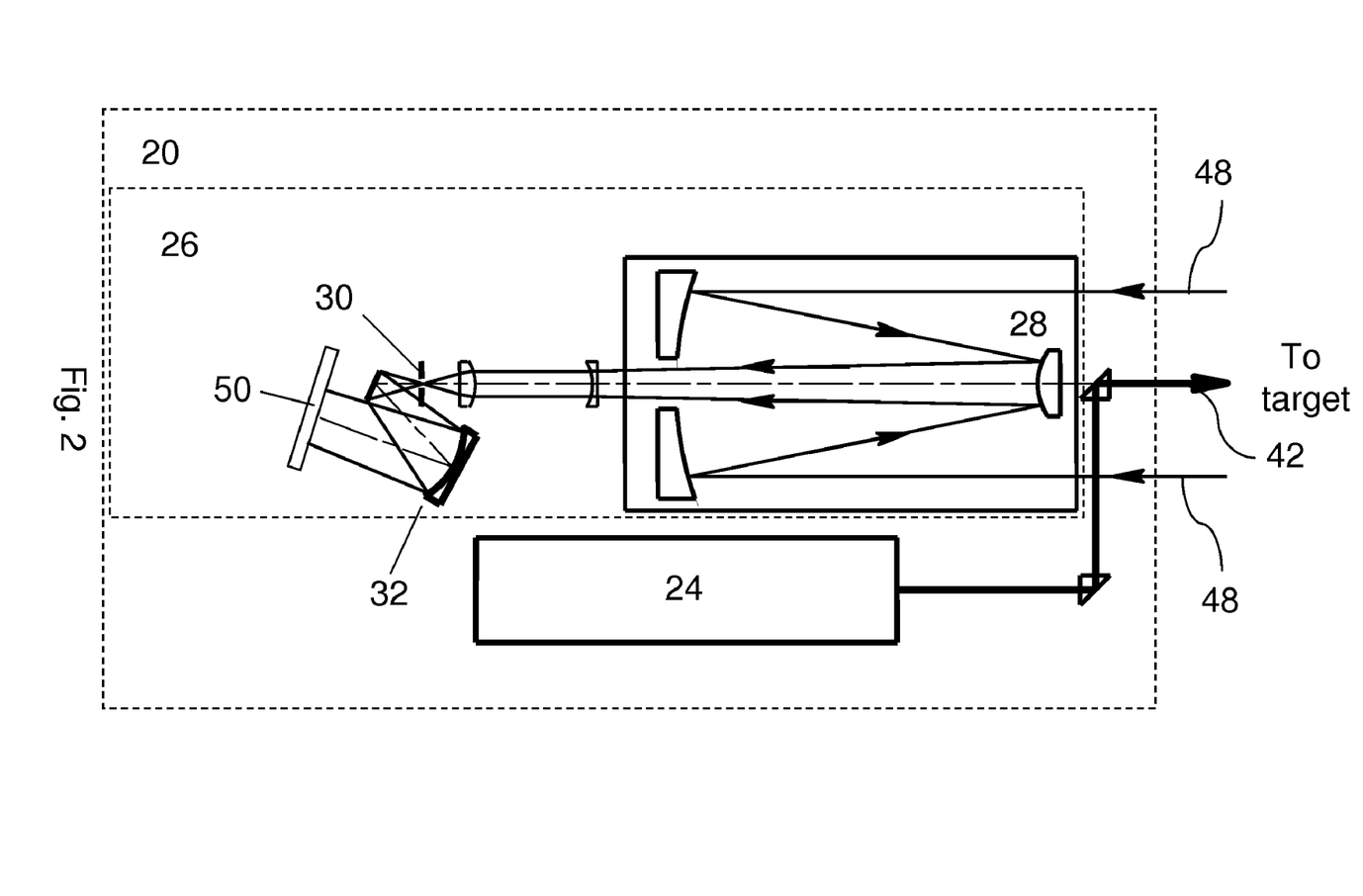
FIG. 2 illustrates a LIDAR optical system employable for some embodiments of this invention.
Figure 3:
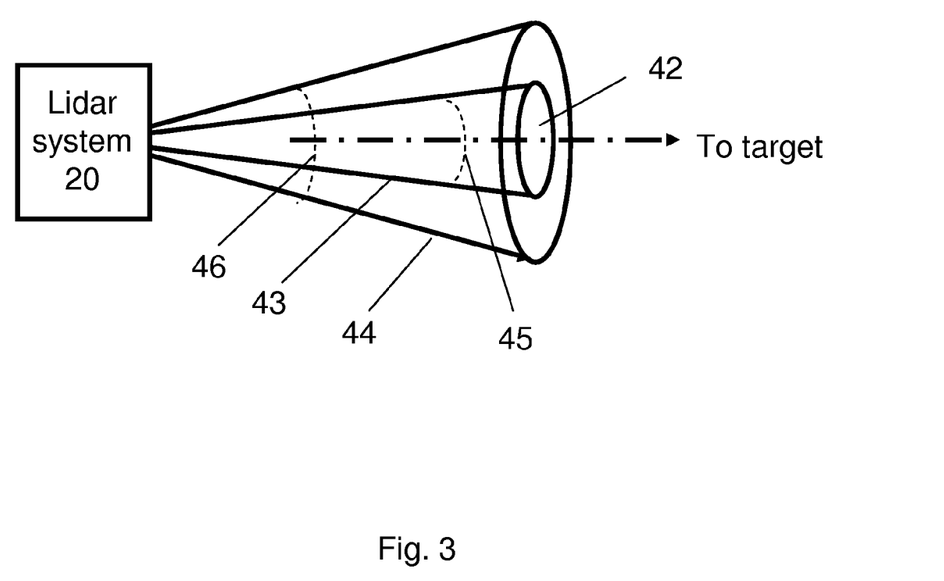
FIG. 3 illustrates schematically a laser beam divergence in relation to the field of view of an optical system employable for some embodiments of this invention.

One embodiment of the invention is presented in FIG. 1. A target is illuminated by a light source having a divergence angle less than the field-of-view angle of a receiver optical system (10 in FIG. 1). This is illustrated schematically for a LIDAR system (Light Detection and Ranging) system 20 in FIGS. 2 and 3, but it is to be understood that embodiments of the present invention are not restricted to LIDAR applications and LIDAR optical systems. For example, the technique would be useful for analysis of a radiating gas, liquid, or surface where one wants to spectrally and optionally spatially resolve laser-induced light scattering or emission from background light from the radiating gas, liquid, or surface. Further, the technique is not restricted to pulsed laser excitation but can also be useful in configurations that use pulsed particle beams (such as a pulsed electron beam) to excite a photo-response from a system. It is to be understood that the use of particle beams in the place of light in various embodiments is intended to be included in the scope of this invention. Light 42 from a collimated light source (for example, a laser) illuminates a target. The target can be solid, liquid, gas, or plasma. In some embodiments, the target can be a solid surface or an aerosol. As illustrated in FIG. 3, the approximately collimated light 42 diverges to form a narrow cone 43 of light determined by the laser beam angular divergence. The light 42 interacts with the target and generates an optical signal characteristic of the target. Examples of some optical signals include but are not restricted to laser-induced fluorescence and phosphorescence, inelastic light scattering, such as, for example, Raman scattering, and elastic light scattering such as, for example, Rayleigh scattering and Mie scattering. In embodiments employing particle-beam excitation, the optical signal may be fluorescence or phosphorescence resulting from energy transfer from the energetic particle. One example would be electron-beam-induced luminescence. In FIG. 3, the laser beam angular divergence is exaggerated for drawing clarity. The laser-illuminated volume 43 is smaller than the volume 44 lying within the full field of view of the receiver optical system. Thus, the receiver optical system collects laser-light-generated optical signal plus background light from the region 43 illuminated by the laser but only background light from the outer portion of the total volume 44 that the laser does not illuminate. The angular divergence 45 of the laser beam is less than the field of view angle 46 of the system.

Light (48 in FIG. 2) comprising the optical signal from the target and background light enters the receiver optical system 26, comprising a receiver telescope 28, a field stop 30, a grating 32 or prism, and a pixelated detector array 50. In this step 11, the light from the field of view impinges on a field stop 30 and a portion is passed through. The field stop 30 defines the angular dispersion in the vertical direction (along the spatial axis 56 of the detector array). In the illustrated embodiment, the field stop 30 is also the entrance slit (or entrance aperture) of an imaging spectrometer (employing either a concave grating 32 or a prism for dispersion). The entrance slit 30 limits field angles, and determines (along with the dispersion of the grating and the pixel-to-pixel spacing of the array detector) the spectral resolution in the wavelength-dispersed direction. The detector array 50 is located in the focal plane of the imaging spectrometer, and, as a result, light 48 entering the receiver optical system from a specific field angle is focused onto a specific pixel of the detector array. Along the wavelength axis, the dispersive action of the grating spreads the light of different wavelengths across the array, resulting in the effective loss of angular resolution in that dimension.

For the purpose of description of embodiments of this invention, the horizontal axis is the axis of spectral (wavelength) dispersion. Different wavelengths correspond to different columns of pixels of the detector array. The vertical axis is the axis of spatial or angular dispersion. A single column receives light of the same wavelength but different field angles. Different field angles correspond to different rows of pixels of the detector array. A single row receives light of the same field angle over a range of wavelengths.

Figure 4:
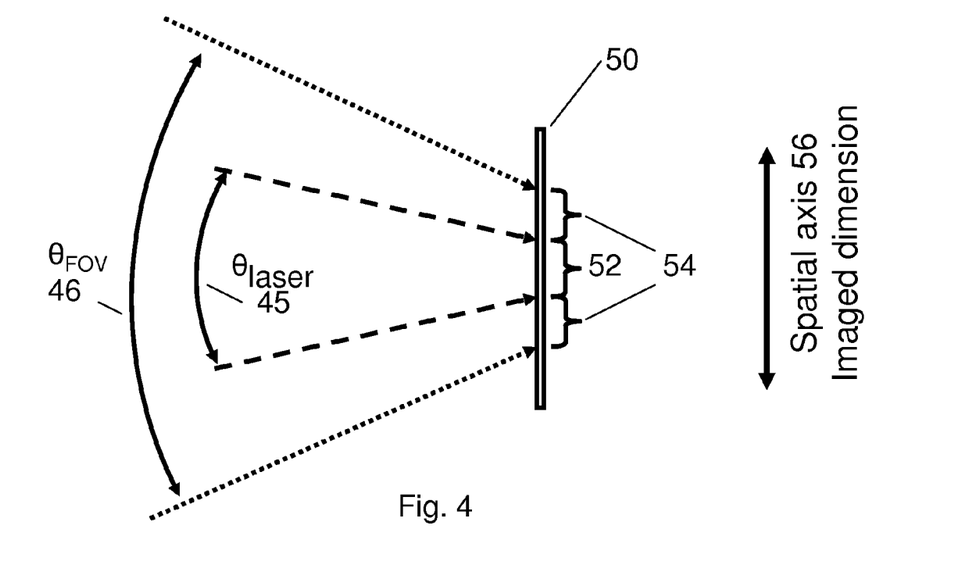
FIG. 4 illustrates schematically the effect of the difference in angular spread for signal light generated by excitation beam interactions with a target (target signal) and for the field of view of a receiver optical system. The different regions of the surface of a detector array that receive background-light only or both target signal and background light are shown in side-view.

FIG. 4 schematically illustrates a side-view of how the laser-generated optical signal and the background-only light interact with the detector array within the receiver optical system. The spatial axis (vertical column direction of the array) is shown. Since the angular range 45 corresponding to the region illuminated by the laser is smaller than the full field-of-view angle 46 of the receiver optical system, light (both target signal and background light) from the laser-illuminated region falls on a central portion (indicated as 52) of the detector array 50. At the same time, background light collected from regions outside the laser-illuminated region falls on outer portions 54 of the detector array. For clarity, we point out that the dashed and dotted "rays" drawn in FIG. 4 are notional rays and not literally the optical rays impinging on the detector array. Input rays to the lidar system 20 (as defined in FIG. 3) map to specific locations in the focal plane 50 as $d \approx f^*\theta$ where d is the position on the array 50, f is the equivalent focal length of the optical system 20, and $\theta$ is the input angle to the optical system 20 as defined in FIG. 3.

Figure 5:
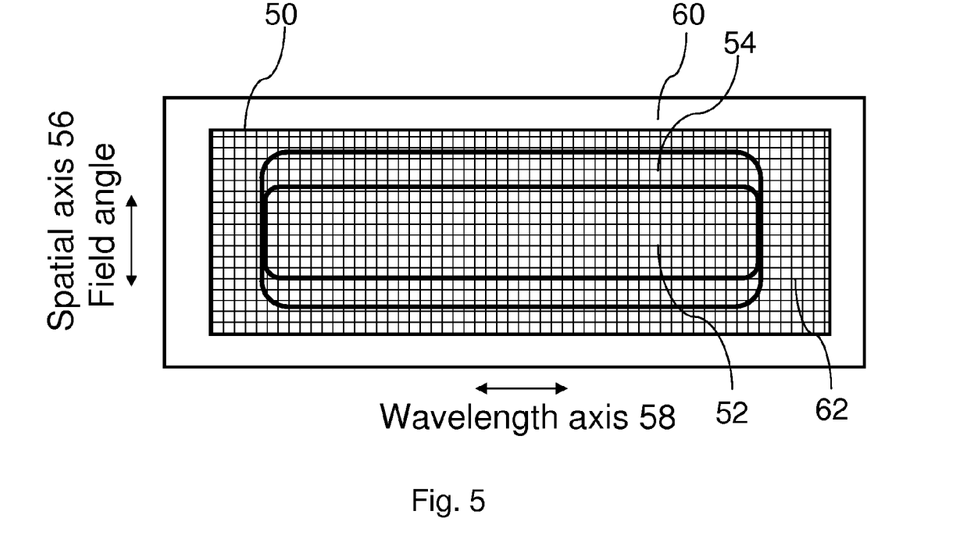
FIG. 5 illustrates schematically the different regions of the surface of a detector array that receive background-light only or both target signal and background light in plan view.

FIG. 5 presents a plan view of the detector array 50 schematically showing a portion of the pixels of the detector array. The pixels are not drawn to scale. The detector array has a spatial axis 56 that receives an image of the vertical dimension of the field stop 30. The geometry of the field stop can be different in different embodiments. In some embodiments, the field stop is a pinhole. In other embodiments, the field stop is an elongated opening, such as a slit. When the field stop is a slit, there are an increased number of pixels illuminated by the background light only, which can improve the signal-to-noise of the background-only light measurement. The detector array also has a wavelength axis 58 along which the incoming light has been spectrally dispersed by a grating 32 or prism. As illustrated in FIG. 5, a column 60 of pixels corresponds to a given wavelength. Within that column, a set of the pixels 52 will receive both target-associated signal light and background light. Within the same column, there will be other sets of pixels 54 that receive background light from within the field of view of the receiver optical system. There may also be additional pixels 62 that are not illuminated and can provide a measurement of the dark noise of the detector array.

Due to laser positional jitter and/or pointing jitter in the receiver optics (such as may be caused by environmental effects such as vibration or temperature variations), there may be some pixels in a column located between the target-associated pixels and the background pixels that sometime receive light from the target and sometime do not. In such embodiments, where certain pixels neither always receive light from the laser-illuminated region nor always receive only background light, signal from such pixels may be excluded from the background subtraction analysis.

For simplification of the description, it is assumed that the detector array is aligned with respect to the field stop (for example, the entrance slit to the spectrograph) and the grating or prism such that the angularly (spatially) dispersed light of a give wavelength aligns parallel to the columns of pixels in the detector array. In the event of some misalignment from parallel, embodiments of this invention would compensate such that the pixels corresponding to a given wavelength, whether they were in one column or in sections of two or more adjacent columns, can be employed for determining appropriate background and target signals.

In some embodiments of this invention, the background-corrected signal is obtained as follows. Herein, we use the term laser to include both lasers and optical sources with sufficiently small divergence to functionally serve as a substantially collimated light source. The incoming light 48 is collected and focused to pass through a field stop 30 (an elongated aperture, slit, or pinhole, for example) and spectrally dispersed to form a spectrum, with the detector array direction corresponding to the spectral dispersion being termed a row. Each pixel in a row corresponds to a wavelength or narrow band of wavelengths. The array direction perpendicular to the spectral direction corresponds to the angular dispersion of the incoming light, with the detector array direction corresponding to the spatial (angular) dispersion being termed a column. In the following discussion, we refer to this direction as the spatial or angular direction. Individual pixels in a column each correspond to a field angle within the total field of view. The spatial extent of target signal at the detector plane of the detector array is defined by the angular extent of the laser beam (divergence) while the dimension of the entrance aperture of the spectrometer (which is the field stop for the optical system) determines the overall field of view that the detector observes. When the detector is at the back focal plane of the receiver optical system (or imaged to that plane), the spatially resolved direction is also angularly resolved. Position in the y-direction, i.e., along a column of pixels, maps directly to a field angle of the receiver optical system. A pixel signal that comprises both optical signal from the target of interest and background illumination contributions is obtained from each pixel that has been assigned as a element of a first set of pixels that are target-signal pixels, which are those pixels that receive light from within the laser-illuminated region, which is determined by the laser divergence angle. At the same time (substantially within one array read-out cycle or alternatively within the time of one or more array read-out cycles during a single laser pulse), a pixel signal that comprises background illumination contributions but not optical signal from the target of interest is obtained from each pixel of a set of pixels that have been assigned as an element of a second set of pixels. The second set of pixels are pixels that are within the field of view of the receiver optical system and correspond to angles that are less than or equal to the field of view of the receiver optical system in the spatial direction but are also greater than the laser beam divergence. These pixels receive only background illumination. There may be a set of pixels positioned within the pixel column for a given wavelength that are situated between the first set and the second set which, due to variation in laser beam characteristics and optical system alignment jitter, sometimes receive target optical signal and sometimes do not. These pixels can be excluded from the target pixel set and the background pixel set if so desired for subsequent analysis.

Depending on the overlap of the field of view with the pixel array, there may be an additional set of pixels 62 toward the edge of the array that are outside the receiver optical system field of view and which contain dark-noise signal but not signal originating from light that has entered the receiver optical system from its field of view. These pixels are not included in the generation of the background-corrected target signal but may be used to correct the signals for dark-noise signal if so desired.

To obtain a background-corrected target signal, for a given wavelength, the output of a plurality of pixels 52 in a column corresponding to that wavelength that receive light (target-derived signal and background illumination) from the region defined by the laser beam divergence are summed to provide a target-signal-plus-background measurement. The summation may be over a single column or over a plurality of columns, depending on the wavelength resolution of the spectrum that is desired. The output of a plurality of pixels 54 in the same column that receive only background illumination are separately summed during the same read-out cycle or during the same laser pulse to provide a background measurement. In many embodiments, the total number of pixels contributing to the background measurement and to the target-signal-plus-background measurement will be different. In addition, the illumination of detector array may not be uniform in the spatial direction due to the angularly varying response of the receiver optical system. To provide a suitable background value for subtraction, a weighting factor is multiplied by either the background signal or the target-signal-plus-background signal to provide proper scaling to account for the different numbers of pixels and the differing response of individual pixels to uniform illumination that contribute to each type of measurement. Factors that may affect the selection of a suitable weighting factor are the non-uniformity of the laser beam excitation and the non-uniformity of the receiver optical system response function.

In some embodiments, the following method of passive baseline correction may be employed. The procedure is illustrated in this embodiment with field test data obtained using an intensified charge-coupled device (ICCD) array detector coupled to an imaging spectrometer in a LIDAR system. In some embodiments, one may record a detector dark baseline with no light incident on the detector. This enables determination of spatially varying offsets (due to dark current and/or digitizer and readout levels) that may be employed in later analyses. For some types of array detectors, such as ICCD arrays, such offsets can be extremely reproducible over both short and long time scales. While the embodiment discussed below as an example of this invention employs an ICCD array detector, other types of detector arrays may be employed in different embodiments. The dark baseline can be measured before or after collection of signal data, as convenient and/or appropriate.

Figure 6:
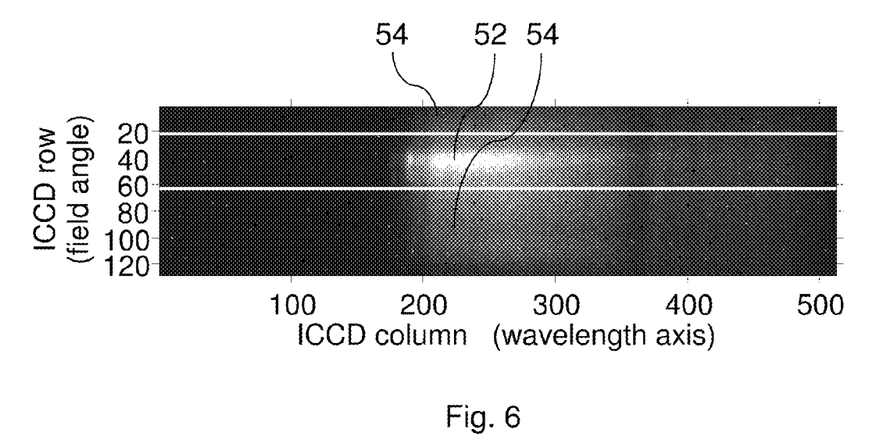
FIG. 6 illustrates image on an ICCD detector array located at the focal plane of the spectrometer of a LIDAR system. The horizontal cursor lines (at rows 23 and 63) indicate the region used as the target signal region.

In order to properly subtract the passive background from the 2-D focal plane images acquired with the detector array, one identifies those regions 54 of the detector array that receive only passive background light and those regions 52 that receive target optical signal plus background light. The ICCD image in FIG. 6 shows an example of a focal plane image. The column numbers correspond to different wavelengths (as the wavelengths are dispersed along this dimension of the array) and the row numbers correspond to different angular (or spatial) directions. The two white lines show the demarcation of the outer regions 54 of the array that contain passive background light only (the region above the top line and below the bottom line). The region 52 between the two lines contains both target signal (due to the laser excitation in this example) and passive background.

Often the demarcation between the two regions can be somewhat indistinct since the target signal does not have extremely sharp boundaries and it can also move slightly over the course of a measurement due to laser pointing jitter, other variations in the receiver optical system and variations due to atmospheric blooming, (i.e., changing the laser beam divergence) due to atmospheric turbulence. In addition, the region of target signal plus background light can move slowly over time due to slow alignment drift between the laser and the LIDAR optical receiver components (such as, for example, mirror mount shifting slightly due to temperature variations). As a result, it may sometimes be desirable to occasionally determine the location of the regions more than once during the course of multiple measurements.

In some embodiments, one may determine the demarcation between the regions of interest as follows. One can measure the target signal in the absence of the background. For example, one can measure the laser-induced fluorescence of a target during substantially complete darkness (for example, at night). While this is a simple method, it often will not work well for optical systems such as LIDAR systems that have significant drift in the alignment between the laser and receiver over the time period between when the background-free measurement (night or pre-dawn) and when background subtraction is needed (dawn or daytime) to obtain a background-corrected target signal.

In other embodiments, one can measure the passive background (background light not dependent on or related to active laser emission/excitation) in the absence of laser-induced signal and compare it with data containing passive background plus signal. This approach can be more generally employed since it only requires turning off the laser and recording the background in the absence of laser light. This method can accommodate pointing drift over time as well as changing passive background illumination. This technique is described below.

Vertical cross sections (for example, along columns) are taken through a 2-D spectrogram, like that in FIG. 6. The intensity distribution as a function of field angle of the background light (dotted line in FIG. 6) is obtained in the absence of target contributions. The data plotted as the dotted line represent the average of approximately 30 data collection cycles where the output of pixels in a given row are summed over the spectral region of approximately 225 columns that correspond to elastic scattering and fluorescence bands that one wants to measure. The dashed curve presents the intensity distribution as a function of field angle in the presence of target aerosol and laser excitation and represents the average of approximately 35 data collection cycles. The solid curve in FIG. 6 is the difference between the LIF plus background light and 0.7 times the background signal presented as the dotted line. The background data are scaled because the solar flux was increasing during the data collection and was significantly greater during the background measurement time than during the target data collection time.

These cross sections illustrate both the demarcation between background-only regions and signal-plus-background regions and the variation in intensity vs. field angle that are inherent in any LIDAR or other optical systems. The response of the LIDAR system to uniform illumination (from daylight scattered from the atmosphere in this illustrated case) varies as a function of field angle due to vignetting and other optical processing performed by the receiver optical system.

Figure 7:
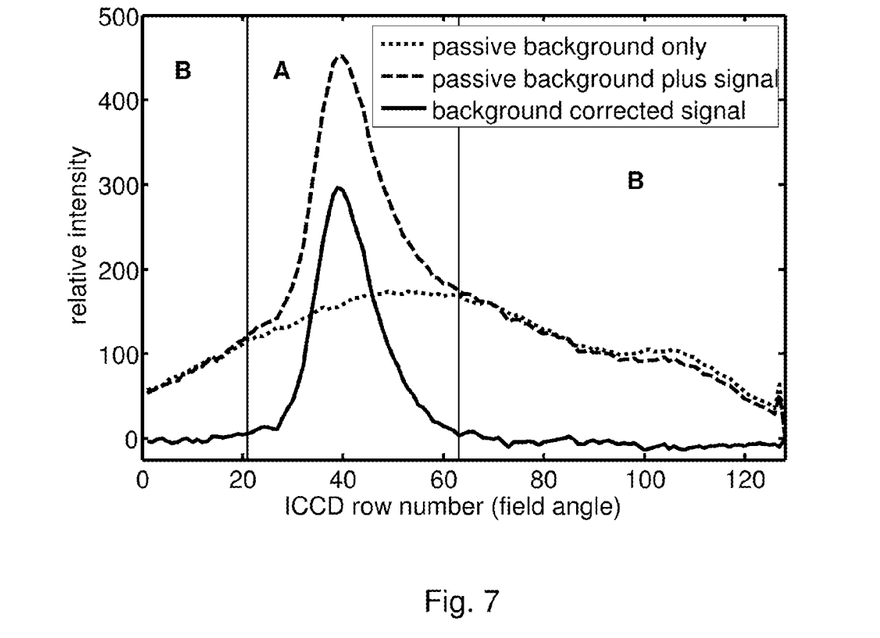
FIG. 7 presents a vertical cross section integrated over several columns corresponding to approximately a 40 nm wavelength range. It illustrates the relative intensity of the background with respect to the receiver field angle.

The dotted curve in FIG. 7 shows a vertical cross section (integrated over a wide wavelength region to improve signal to noise) for a solar-background-only image. This purpose of this cross section is not to provide wavelength information but rather information about the "shape" of the background with respect to receiver field angle. In the embodiment illustrated in FIG. 7, data were selected in which there was no signal due to aerosols. It is equivalent to turning off the laser for a brief period in order to assess the background, which is an alternative method that would often be employed in real field applications of this technology. The dashed curve is a cross section through an image which contains both target signal and passive background (integrated over the same spectral band as the background-only cross section). The two curves are scaled to account for the time-varying intensity of the background light, such as solar background. In this illustrated embodiment, the solar-background-only image was taken at a time when the solar flux was much greater than when the signal-plus-background data was taken. In this embodiment, it is assumed that the response of the optical system (as a function of field angle) is constant over time, so that the shape of the background-only signal is substantially the same, even though its intensity may be changing. If the LIDAR system is viewing clear sky as a background, this assumption is very good. If the LIDAR system is pointed at an inhomogeneous (over the scale of the field of view of the optical system) background, such as the ground, a more sophisticated variation of this method may be employed to separate the background-only regions from the signal-plus-background regions.

If one subtracts the dashed curve from the dotted curve, one obtains the solid curve which is a cross section of the laser-induced signal region. From this solid curve, one can determine the boundaries for the regions of the spectrogram which have passive background only and the region which contains laser-induced target signal in addition to passive background. The vertical cursors show the demarcation of these regions based on this analysis. The region between the two cursors (labeled A) is the region containing both target signal and background and the remaining two regions (labeled B in this example) contain passive background only.

In general, simply subtracting all of the passive-background-only intensity from the target signal plus background intensity may produce a distortion of the background-corrected spectrum since the number of pixels with target signal and with background-only signal are not equal and the response function of the receiver optical system depends on field angle. In some embodiments, a suitable scaling factor is determined as follows. If one assumes that the optical response function vs. field angle is constant over time, one can use the ratio of the integrated background-only intensity in regions labeled A in FIG. 8 to the integrated background-only intensity in regions labeled B. In the example shown here, this ratio is 0.786.

Figure 8:
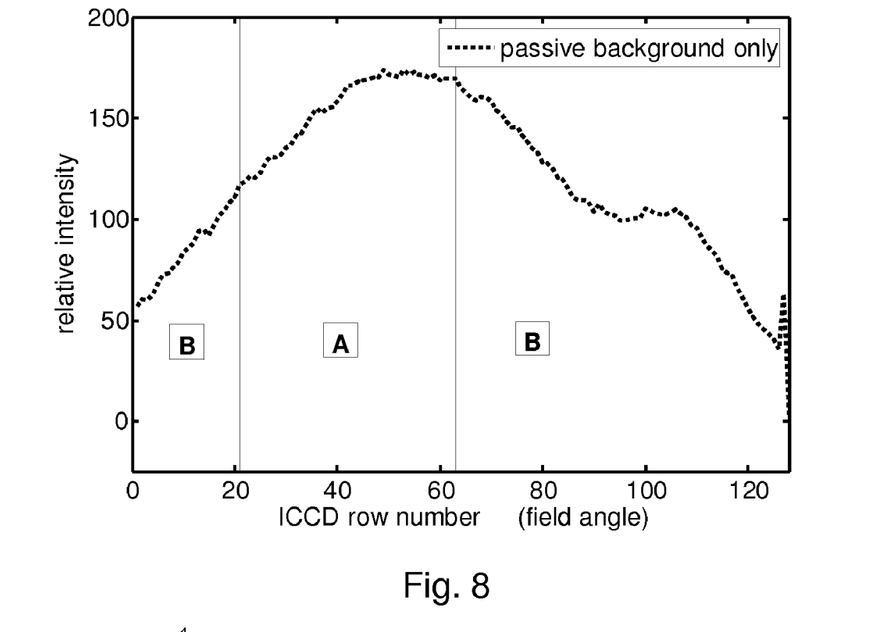
FIG. 8 illustrates the magnitude of the background signal as a function of field angle. The ratio of the integrated intensity corresponding to the target signal pixel set (area labeled A) and the integrated intensities corresponding to the background-only pixel sets (areas labeled B) provides the background signal scaling factor.

If we call the intensity (or value) of the passive-background-only signal at each pixel location $I_b(x, y)$, then the constant C is given by $$C = \frac{\sum_{spectral\ band} \sum_{region\ B} I_b(x, y)}{\sum_{spectral\ band} \sum_{region\ A} I_b(x, y)}$$

where the first sum is carried out over all of the columns in the spectral band of the data and the second sum is carried out over the rows of region B and region A respectively.

In order to correct an ICCD spectrogram for passive background, in some embodiments one takes the 2-D spectrogram and sums all rows in region B, multiplies it by the scaling factor just obtained (0.786 in this case), and subtracts it from the sum of all rows in region A.

If the intensity of a pixel in the image to be corrected is $I(x, y)$, the background-corrected spectrum, $I_c(x)$ is given by $$I_c(x) = \sum_{region\ A} I(x, y) - C \sum_{region\ B} I(x, y)$$

where the sums are over the rows of region A and region B respectively and C is the constant determined in the previous step.

Figure 9:
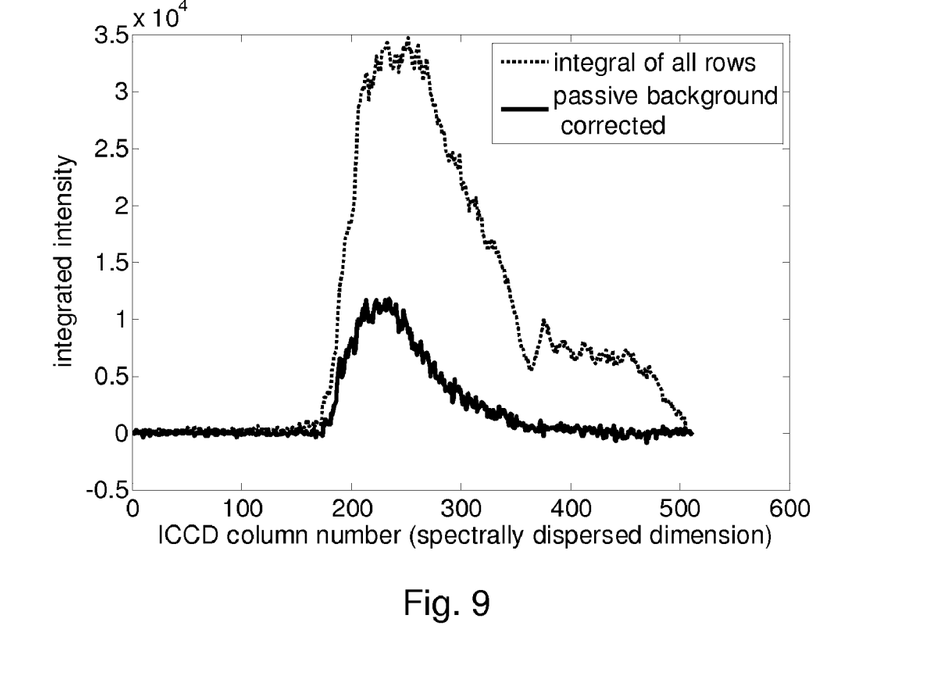
FIG. 9 presents the integrated intensity for each column including target signal and background (dotted line) and the background-corrected target signal (solid line) after subtraction of the scaled contributions from the background-only signal.

An example of applying this correction is shown in FIG. 9. The dotted line shows the spectrum obtained by summing for each column its pixels in all of the rows of the ICCD that within the field of view of the receiver optical system. The solid line is the background-corrected spectrum obtained by using the procedure just described. Note that the LIF spectrum (of ovalbumin in this case) is very different (in shape) from that of the solar background spectrum.

Figure 10:
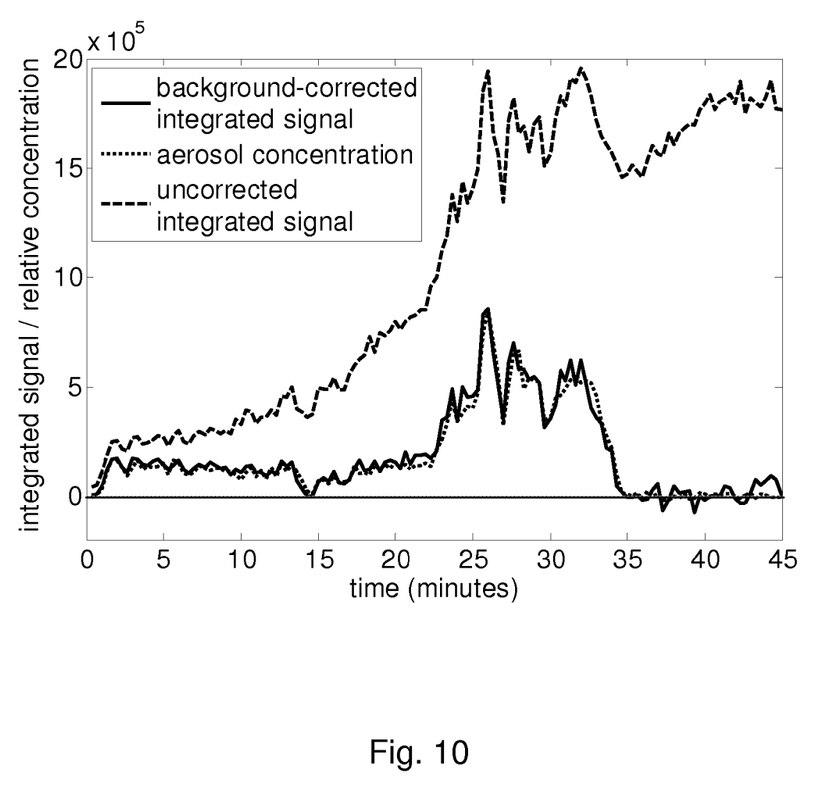
FIG. 10 illustrates a comparison between a time-dependent signal from an aerosol target with (solid line) and without (dashed line) passive background correction and between the background-corrected target signal and an independently measured concentration (dotted line) over time.
Figure 11A:
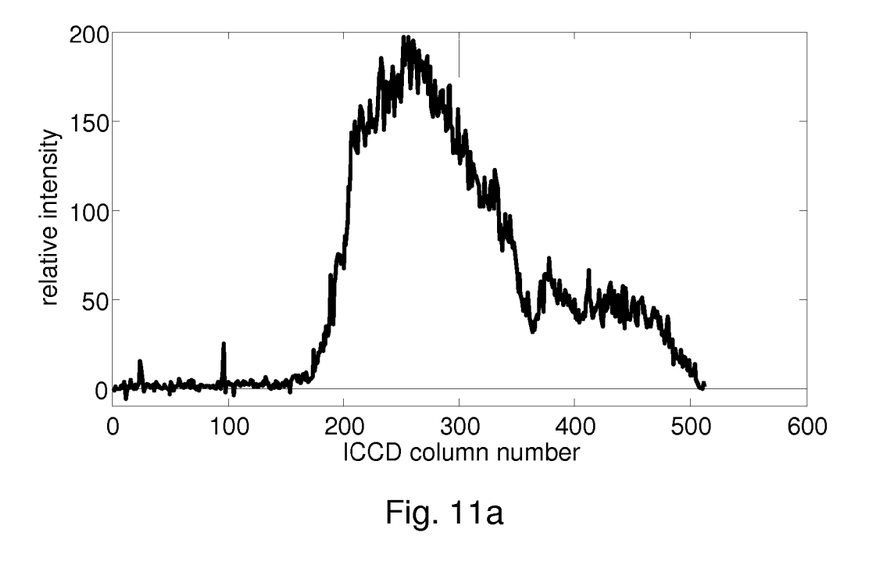
Figure 11B:
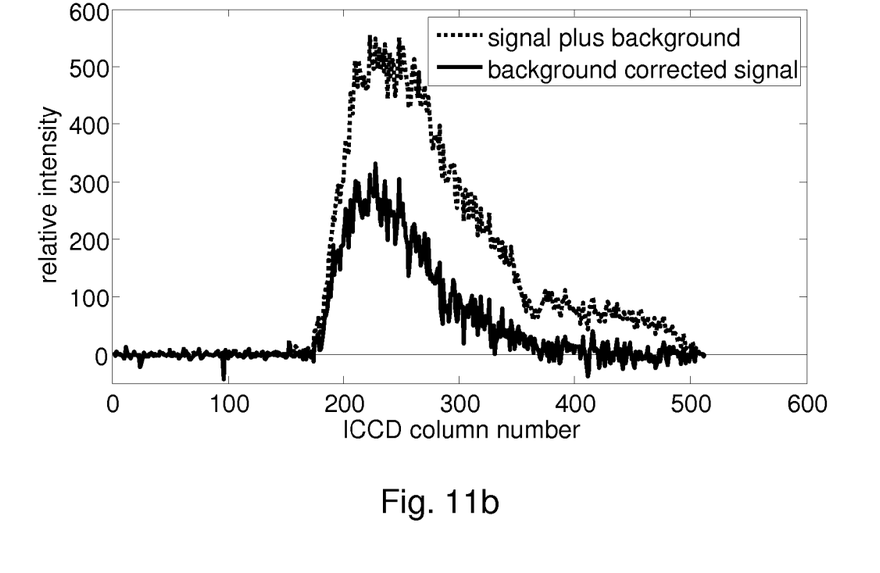

To illustrate how well the correction method works in the example shown here, the spectrally integrated signal over the time span of the test is plotted in FIG. 10. During a field test, the aerosol concentration and the solar background are both changing over time. In FIG. 10, the dashed line shows the uncorrected signal (integrated over a narrow spectral region) vs. time. Note that this test occurred during dawn and the solar background is increasing over time. The solid line shows the background-corrected integrated spectrum over time. Compare this to the dotted line which shows the corresponding aerosol concentration over time. The background-corrected spectrally integrated signal tracks the measured aerosol concentration very well even during times when the ovalbumin concentration was zero and the solar background was high.

Appropriate weighting factors for the signal generated by each individual pixel can be determined and employed to correct the signal intensity from each pixel. For example, the response of the optical system (as a function of row number in the array or field angle in the imaged or non-wavelength-dispersed dimension) can be measured by observing without laser illumination a uniform light source, such the atmosphere if sunlight is the passive background light of concern, and determining the signal variation between rows. The variation of the laser beam intensity versus row number within a column can be measured by illuminating a target (for example, an aerosol in the atmosphere or a hard target such as a Lambertian scattering target) with the laser in the presence of little or no passive background.

In general, the variation of the optical system response should be approximately constant unless changes are made to the optical configuration. The variation in the position of the laser beam can change slightly over both short and long time periods due to laser beam pointing instabilities inherent in practical laser systems. In addition, atmospheric turbulence can cause the effective laser beam divergence to change over the course of the day. In some embodiments, the limits of this laser beam pointing drift can be characterized as described above and adjustments can be made in the weighing factor and in the selection of which pixels contribute to the target-signal-plus-background signal and which contribute to the background-only signal. In practice, the laser beam pointing may change over the course of LIDAR measurements, and corrections may be made in an iterative fashion, with the first correction being based on the normal laser beam pointing and extent. If the beam is determined to have moved slightly, a new correction may be made based on the result of this first iteration.

In some embodiments, the dynamic compensation described above is not employed. In such embodiments, one expands the region of the active signal to encompass all expected pointing instabilities; this may be at the expense of a slightly greater passive background shot noise and a different passive background scale factor but still provides good background correction.

For remote sensing applications of this invention, the time-gating of the detector is chosen so that the signal arising from excitation of the target by the laser pulse will arrive during the gated detector collection time. Gating the detector minimizes the amount of background-only light detected and maximizes the ratio of the laser-induced signal to passive-background-only light.

Many of the previously described embodiments employed pulsed excitation beams. In many embodiments, the use of continuous-wave (CW) excitation sources is possible. The term continuous-wave is applied for purposes of this invention to non-pulsed sources of light, electrons, and/or ions. The approach to background correction of this invention is applicable to CW excitation embodiments.

Another embodiment of this invention involves optical systems that image one region in space to the spectrally dispersed detector array. The notion of field angle as described above corresponds to spatial location in such embodiments. An example may be an imaging dispersed fluorescence diagnostic where a specific region of a sample may be imaged onto the two dimensional array. In an imaging application, the field angle axis (as in FIG. 5) is replaced with a spatial axis, i.e., different spatial locations are imaged to specific locations on the array detector. A specific spatial location will be illuminated with an excitation beam, such as a laser beam, and some regions imaged will not be illuminated with the excitation beam. Those regions not illumination (54 in FIGS. 5 and 6) can be used for background subtraction. For example, when the sample within the imaged region emits due to causes not directly associated with the excitation-beam-caused emission, a passive background can result that may interfere with or degrade the desired excitation-beam-induced emission measurement. In this case, analogous techniques for background correction that have been described above can be used.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for improved background correction for spatially and spectrally resolved detection, comprising:
   illuminating a target region with an excitation beam, wherein a divergence angle of the excitation beam is less than a field-of-view angle of a receiver optical system comprising a detector array;
   collecting on a first set of pixels of the detector array a target region signal generated in part by light produced by an interaction of the excitation beam with a target, wherein the first set of pixels of the detector array is determined by the divergence angle of the excitation beam;
   collecting at the same time on a second set of pixels of the detector array a background signal generated substantially by background light; and
   correcting the target region signal using the background signal to obtain a background-corrected target signal,
   wherein the first set and the second set comprise sections of a column of pixels of the detector array corresponding to a same wavelength.

2. The method of claim 1, wherein the excitation beam is selected from the group consisting of a light beam, an electron beam, and an ion beam.

3. The method of claim 1, wherein the excitation beam is selected from the group consisting of a pulsed excitation beam and a continuous-wave excitation beam.

4. The method of claim 1, wherein the second set of pixels consists of a set of pixels illuminated by light from within a field of view of the receiver optical system but not illuminated by light produced by the interaction of the excitation beam.

5. The method of claim 1, further comprising:
   collecting at the same time on a third set of pixels of the detector array a dark-noise signal, wherein the third set of pixels consists of at least one section of pixels of the detector array not illuminated by light originating from within a field of view of the receiver optical system; and
   correcting the background signal using the dark-noise signal to generate a dark-noise-corrected background signal.

6. The method of claim 1, wherein the background-corrected target signal is selected from the group consisting of beam-induced fluorescence, beam-induced phosphorescence, and beam-induced luminescence.

7. The method of claim 1, wherein the excitation beam is a laser.

8. The method of claim 7, wherein the background-corrected target signal represents light selected from the group consisting of laser-induced fluorescence, absorption, inelastically backscattered light, Raman scattering light, elastically scattered light, Rayleigh scattering light, and Mie scattering light.

9. The method of claim 7, wherein the receiver optical system is a lidar optical system.

10. The method of claim 1, wherein the target comprises at least one of a solid surface and an aerosol cloud.

11. The method of claim 1, wherein the target comprises at least one of a solid, a liquid, and a gas.

12. The method of claim 1, wherein the detector array is selected from the group consisting of a CCD array, an intensified CCD array, an electron multiplying CCD array, an avalanche photodiode array, a silicon photodiode array, a CMOS array, and a multi-anode photomultiplier tube.

13. A method for improved background correction for spatially and spectrally resolved detection, comprising:
   illuminating a target region with an excitation beam, wherein a divergence angle of the excitation beam is less than a field-of-view angle of a receiver optical system comprising a detector array;
   collecting on a first set of pixels of the detector array a target region signal generated in part by light produced by an interaction of the excitation beam with a target, wherein the first set of pixels of the detector array is determined by the divergence angle of the excitation beam;
   collecting at the same time on a second set of pixels of the detector array a background signal generated substantially by background light;
identifying pixel element rows of the first set of pixels and of the second set of pixels, the steps of identifying comprising:
   summing row-wise outputs of row pixels spanning a wavelength range with the excitation beam being off during the summing to determine a background field-angle intensity average for each pixel row;
   summing row-wise the outputs of row pixels spanning the wavelength range with the excitation beam being on during the summing to determine an excitation field-angle intensity average for each pixel row;
   scaling the background field-angle intensity average to obtain an approximate best match with the excitation field-angle intensity average for a set of pixel rows spanning a field-angle range to obtain a scaled background field-angle intensity average;
   subtracting the scaled background field-angle intensity average from the excitation field-angle intensity average to obtain a background-corrected field-angle intensity average;
   examining the background-corrected field-angle intensity average to identify target region pixel rows and background pixel rows; and
   assigning pixels from target region pixel rows to the first set of pixels and pixels from the background pixel rows to the second set of pixels; and
   correcting the target region signal using the background signal to obtain a background-corrected target signal,
wherein the first set and the second set comprise sections of a column of pixels of the detector array corresponding to a same wavelength.

14. The method of claim 13, further comprising determining a background scaling factor by
   summing column-wise intensity signals from the background pixel rows to obtain a background region intensity;
   summing column-wise intensity signals from the target region pixel rows to obtain a target-region intensity; and
   dividing the target-region intensity by the background-region intensity to obtain the background scaling factor, wherein during the determining of the background scaling factor the excitation beam has insufficient power to produce a target signal or is off.

15. The method of claim 1 further comprising determining a background scaling factor by
   summing column-wise intensity signals from the background pixel rows to obtain a background region intensity;
   summing column-wise intensity signals from the target region pixel ws to obtain a target-region intensity; and
   dividing the target-region intensity by the background-region intensity to obtain the background scaling factor, wherein during the determining of the background scaling factor the target is substantially absent from the target region.

16. The method of claim 1, wherein the step of correcting the target region signal using the background signal comprises:

summing column-wise outputs of target region pixel rows to obtain a summed target region intensity;

summing column-wise outputs of background pixel rows to obtain a summed background region intensity;

multiplying the summed background region intensity by a background scaling factor to obtain a scaled background intensity; and subtracting the scaled background intensity from the summed target region intensity to obtain the background-corrected target signal.

* * * * *